United States Patent
Bucha et al.

(10) Patent No.: US 7,494,824 B2
(45) Date of Patent: Feb. 24, 2009

(54) INTERACTIVE SYSTEM FOR PRESENTING AND ELIMINATING SUBSTANCES

(75) Inventors: Elke Bucha, Erfurt (DE); Götz Nowak, Erfurt (DE)

(73) Assignee: Max-Planck-Gesellschaft zur Förderung der Wissenschaften e. V., Berlin, München (DE)

(*) Notice: Subject to any disclaimer, the term of this patent is extended or adjusted under 35 U.S.C. 154(b) by 504 days.

(21) Appl. No.: 11/170,666

(22) Filed: Jun. 29, 2005

(65) Prior Publication Data

US 2005/0239131 A1    Oct. 27, 2005

Related U.S. Application Data

(62) Division of application No. 09/417,534, filed on Oct. 14, 1999, now Pat. No. 6,929,955.

(30) Foreign Application Priority Data

Apr. 14, 1997    (DE) ................. 197 15 504

(51) Int. Cl.
*G01N 33/545*    (2006.01)
(52) U.S. Cl. .............. 436/531; 436/518; 436/523; 436/524; 436/528; 436/529; 436/530; 436/532; 436/533; 436/534; 436/535; 436/161; 436/162; 436/169; 436/170; 436/175; 436/178; 435/7.92; 435/180; 435/181; 424/1.29
(58) Field of Classification Search ................. 436/518, 436/523, 524, 528, 529–535, 161, 162, 166–169, 436/178, 823; 435/7.92, 30, 177, 180, 182, 435/187.7, 287.8, 287.9, 288.6; 424/1.29, 424/1.33, 1.41, 1.49
See application file for complete search history.

(56) References Cited

U.S. PATENT DOCUMENTS

| | | | |
|---|---|---|---|
| 3,884,761 A | | 5/1975 | Cowling |
| 4,086,199 A | * | 4/1978 | Daniel ................... 523/201 |
| 4,207,200 A | | 6/1980 | Müller et al. |
| 4,575,539 A | * | 3/1986 | DeCrosta et al. ........... 524/458 |
| 5,410,016 A | * | 4/1995 | Hubbell et al. ............. 528/354 |
| 5,453,461 A | | 9/1995 | Heiliger et al. |
| 5,665,428 A | | 9/1997 | Cha et al. |
| 5,752,974 A | | 5/1998 | Rhee et al. |
| 5,795,719 A | | 8/1998 | Richard et al. |

FOREIGN PATENT DOCUMENTS

| | | |
|---|---|---|
| CA | 1069070 | 1/1980 |
| CA | 1 335 142 | 4/1995 |
| DE | 27 12 344 | 9/1978 |
| EP | 0 345 780 B1 | 12/1989 |
| EP | 0 459 632 A1 | 12/1991 |
| EP | 0 591 807 A2 | 4/1994 |
| EP | 0 700 933 A1 | 3/1996 |
| FR | 2 332 287 | 6/1977 |
| GB | 1 218 620 | 1/1970 |
| GB | 1 484 564 | 9/1977 |
| WO | WO 92/07882 A1 | 5/1992 |
| WO | WO 92/07023 A1 | 7/1992 |
| WO | WO 93/18649 A1 | 9/1993 |
| WO | WO 94/25503 A1 | 11/1994 |

* cited by examiner

*Primary Examiner*—Gailene R Gabel
(74) *Attorney, Agent, or Firm*—Panitch Schwarze Belisario & Nadel LLP

(57) ABSTRACT

An interactive system is provided with at least one active surface of plastic from monomers containing at least one structural element derived from a carbon dioxide (A), and at least one substance associated to a linker with at least one structural element (B) capable of establishing a hydrogen bond, and involving an interaction between the structural elements (A) and (B). The interactive system is suitable for presenting and eliminating substances in liquids.

18 Claims, 4 Drawing Sheets

INTERACTIVE SYSTEM FOR PRESENTING AND ELIMINATING SUBSTANCES

CROSS-REFERENCE TO RELATED APPLICATION

This application is a divisional of U.S. patent application Ser. No. 09/417,534 filed Oct. 14, 1999, issued as U.S. Pat. No. 6,929,955 B2 on Aug. 16, 2005, which in turn is a continuation of International Application No. PCT/EP98/002183, the disclosures of which are incorporated herein by reference.

BACKGROUND OF THE INVENTION

The present invention relates to interactive systems for presenting and eliminating substances in liquids. Furthermore, the invention relates to devices manufactured with these interactive systems such as for example capillary tube systems, fiber material for filtering physiological liquids, filter mats, arthroplasties or vascular prostheses, etc.

For a number of purposes it is often necessary to eliminate specific substances from a liquid or to present substances in a liquid.

For instance, physiologically active substances are frequently coupled with polyalkylene glycols, e.g. polyethylene glycol, in order to increase the molecular weight and thus improve the pharmacokinetics in the body (cf. e.g. Thrombosis and Haemostasis, 77 (1), 168-73 (1997), Peptide Research, Vol. 8, No. 2 (1995)). Such substances are widely used in therapy nowadays. So far, for such substances no effective functional antidotes, or systems which neutralize their effects, i.e. systems for eliminating these substances, are available.

During serious diseases, cellular signal substances from a functional disorder are often passed into the bloodstream, which enables these cellular signal factors to spread rapidly to any part of the body. This can cause both useful responses by the organism to such signals, but also frequently pathological ones. By neutralizing or blocking these pathogenic factors, a disease can be interrupted or the progress of a disease can be warded off so that the body's own repair mechanisms are given the opportunity to intervene.

Typical examples of such signal substances are the cellular messengers of the endothelial and circulating blood cells such as e.g. CD1, CD2, CD6, CD8, CD16, tumor necrosis factor (TNF) etc. Induced proteins which are pathogenically significant such as e.g. the lipoprotein-binding protein LBP are also responsible for the development of extremely serious complications with patients in septic shock.

It would be important to be able to gently eliminate such substances via an extracorporal therapeutic system without burdening the organism with further substances. Furthermore, it would be advantageous to treat certain diseases with systems for presenting monoclonal antibodies or fragments of these monoclonal antibodies. At this time, such a therapy is only possible for a limited period of time since the immunocompetent cells of the organism quickly produce human antibodies against these foreign proteins. A local presentation of such monoclonal antibodies in the blood circulation can be applied to neutralize antigens in the blood for a long time without causing any immunoreactivity.

Moreover, it is often desirable to eliminate certain ingredients in foodstuffs, such as e.g. cholesterol, certain fatty acids, alcohol, impurities of a microbial or bacterial nature etc. gently and easily, for instance in order to produce specific foods for special dietary requirements.

BRIEF SUMMARY OF THE INVENTION

The object underlying the present invention is therefore to provide a simple inexpensive and universally applicable system for the elimination or presentation of substances in a liquid. The system should be easy to adapt to various practical requirements. Furthermore, the system should not adversely affect the liquid or environment to be treated and should be easy to remove therefrom. If the system is used for diagnostic and therapeutic purposes it should be applicable in a gentle manner and not put any burden on the body.

This object is achieved according to the present invention by an interactive system comprising at least one active surface of a plastic material from monomers containing at least one structural element (A) derived from a carboxylic acid and at least one substance coupled to a linker with at least one structural element (B) capable of establishing a hydrogen bond, the interaction taking place between the structural element (A) and (B). Preferably, the structural element derived from a carboxylic acid is located in the side chain of the monomer. More preferably, the plastic material comprises the structural element

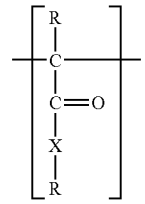

wherein the groups R can be the same or different and represent any alkyl or aryl group or a hydrogen atom. X is an optional group and represents O, N or $CH_2$.

Surprisingly, it was found during examinations of the bonding capacity of surface structures that surfaces of a plastic material from monomers containing at least one structural element (A) derived from a carboxylic acid enter a very stable interaction with linkers with at least one structural element capable of establishing a hydrogen bond. Such an interaction is very stable and cannot be reversed for example by pH values from 2 to 13 or buffers having a high ionic strength or temperatures up to +60° C. This interaction can be used for coupling a wide range of substances by coupling the substances to this linker after which the substances enter a corresponding interaction with the plastic material. Active surfaces can be produced from such plastic materials, i.e. surfaces where a corresponding interaction and subsequent reaction of the coupled substance with a co-reactant takes place. This surface may be of any shape and dimension. It is preferably a membrane, a porous or solid microparticle, a magnetic microparticle, a spun material or a coating made from a natural or synthetic substance. Combinations are also possible. For instance, microparticles may be woven into fiber material or associated therewith. This results in a net/framework structure which prevents sagging or compressing of the microparticles, e.g. in chromatography columns. This active surface can be incorporated in various forms in systems such as capillary tube systems, filters for physiological liquids, hemodialysis apparatuses, physiological replacement fluids, enzyme delivery systems, arthroplasties or vascular prostheses or artificial organs. For example, porous microparticles can be applied as an active surface on conventional tube and filter systems. Any desired universally applicable system can be created. By way of simple priming, substances, which may be difficult to couple by means of a covalent bond, can often be easily applied on the corresponding surfaces. This is particularly advantageous if apparatuses or related equipment have to be sterilized. It is often difficult to sterilize covalently bound substances without damaging them. In the present invention, the plastic surface and, at the same time, the substance coupled to a linker can be sterilized and then both sterile components can again easily be brought into interaction under sterile conditions.

Together with the substance coupled to a linker with at least one structural element capable of establishing a hydrogen bond, an interactive system is formed. The interactive system can be present separately, i.e. in different phases, or as a reactive unit. Furthermore, the active surface can also be spun to form hollow fibers, yarns, pressed sheets, filter mats, non-woven fabrics or the like. If the active surface is present in the form of microparticles, they may be of any desired shape, e.g. spherical, diamond-shaped, dumbbell-shaped, rhomboid etc. However, they are preferably spherical with a diameter of 0.5 to 500 µm, preferably 1 to 300 µm, more preferably 1 to 250 µm. Preferably, the microparticles are porous and thus have a larger surface.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
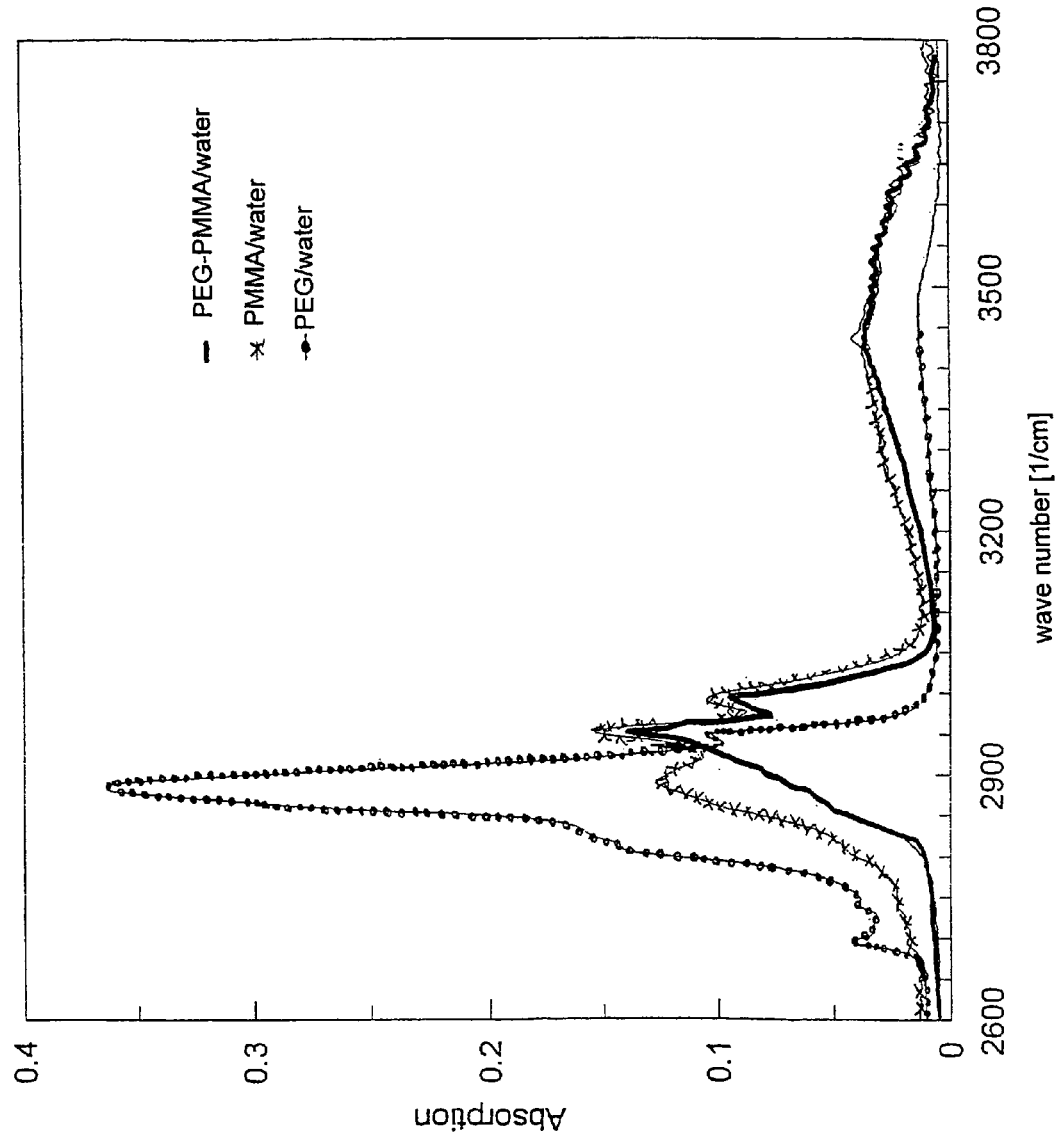
FIG. 1 is a representation of infrared spectra of polymethylmethacrylate, polyethylene glycol (5000) and PMMA-PEG interactive particles.

According to the present invention, the plastic material comprises at least the structural element (A)

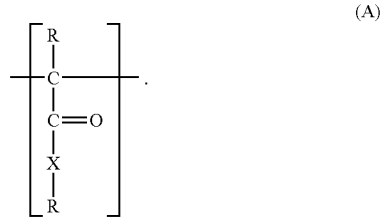

(A)

This structural element is for example part of a polymer of the general formula (I)

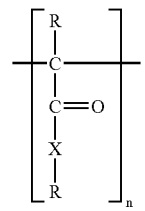

(I)

wherein R represents an alkyl or aryl group or a hydrogen atom and n is 10 to 10,000. The group X is optional and represents O, N or CH$_2$.

The alkyl group may be any straight-chain or branched, optionally substituted, alkyl group. A straight-chain or branched, optionally substituted, C$_{1-8}$ alkyl group, such as for example a methyl, ethyl, n-propyl, i-propyl, n-butyl, i-butyl, s-butyl or t-butyl group is preferred. Examples of optional substituents include one or more halogen atoms, e.g. fluorine, chlorine, bromine or iodine atoms, or hydroxy groups, alkyl groups such as C$_{1-6}$ alkyl groups or alkoxy groups, such as e.g. C$_{1-6}$ alkoxy groups, e.g. C$_{1-3}$ alkoxy, such as methoxy or ethoxy groups, or thiol groups, such as for example C$_{1-6}$ alkylthio groups, e.g. C$_{1-3}$ alkylthio groups, such as methylthio or ethylthio groups. The aryl group can be a monocyclic or bicyclic, optionally substituted aryl group which may optionally contain one or more heteroatoms. Examples thereof are phenyl, 1- or 2-naphthyl, indenyl or isoindenyl groups. Optionally, the aryl groups can also be substituted. Examples of heteroatom-containing aryl groups are a C$_{1-9}$ heteroaryl group, e.g. an optionally substituted C$_{3-9}$ heteroaryl group containing for example one, two, three or more heteroatoms selected from oxygen, sulfur or nitrogen atoms. Monocyclic heteroaryl groups include for example pyrolyl, furyl, thienyl, imidazolyl, N-methylimidazolyl, N-ethylimidazolyl, oxazolyl, disoxazolyl, thiazolyl, isothiazolyl, pyrazolyl, 1,2,3-triazolyl, benzofuryl, isobenzofuryl, benzothienyl, isobenzothienyl, indolyl, isoindolyl, benzimidazolyl, benzothiazolyl, chinazolinyl, naphthylpyridinyl, quinolinyl, isoquinolinyl and tetrazolyl groups.

The tacticity of the thus obtained polymer can be as desired, for example isotactic, heterotactic or syndiotactic.

The linker comprises at least one structural element (B) capable of establishing a hydrogen bond. This structural element can be any polar hydrogen atom, as it is present e.g., in OH, SH, NH or PH bonds. The linker can have any desired chain length. Preferably, the linker is a (poly)alkylene glycol, more preferably polyethylene glycol. Furthermore, a (poly)alkylene imine, a (poly)alkylene amine, a (poly)alkylene sulfide or a polyoxazilin is preferred. The linker can also comprise several of structural elements (B).

The coupling of the substances to the linker takes place according to known processes. For this purpose, reactive derivatives such as for example succinimidyl succinate, succinimidyl propionate, nitrophenyl carbonate, tresylate, epoxides, aldehydes, isocyanates, maleimides and the like can be used. In this connection, reference is made to the catalog of the company Shearwater Polymers, Inc., 2307 Spring Branch Rd., Huntsville, Ala. 35801 (USA).

The plastic material is preferably a polymethacrylate, preferably a polyalkyl(meth)acrylate (PAMA) plastic or a polyalkyl(meth)acrylate copolymer. Especially preferred is the plastic polymethyl(meth)acrylate (PMMA), polyethyl(meth)acrylate (PEMA), polypropyl(meth)acrylate, polybutyl (meth)acrylate (PBMA), polypentyl(meth)acrylate, polyvinyl acetate, polycyclohexyl(meth)acrylate or polyphenyl (meth)acrylate.

Also preferred are mixtures in any ratio of the above-mentioned polyalkyl(meth)acrylates and one or more additional polymer components, for example polystyrene, polyacrylonitrile, polycarbonate or polysulfone. Examples of preferred mixtures include polymethylmethacrylate+polystyrene, polymethylmethacrylate+polyacrylonitrile+methacrylate, polymethylmethacrylate+polyacrylonitrile+methallylsulfonate, polymethylmethacrylate+polyethylenepolyvinyl alcohol, polymethylmethacrylate+polyamide, polymethylmethacrylate+polysulfone. Preferably, the polymethylmethacrylate content in the mixed polymers is at least 20%, more preferably, polymethylmethacrylate accounts for 40% or 60% of the plastic material. Also, mixed polymers can be produced from the known exemplary polymer components.

These mixed polymers can be produced according to methods known in the technical field. Further components can be incorporated into the polymer, e.g. inorganic compounds such as e.g. magnetic or paramagnetic iron compounds or iron, or surface-active substances such as e.g. NO-cleaving compounds such. as e.g. sodium nitronitroprussiate dihydrate. Furthermore, doping with metal atoms such as e.g. nickel, zinc, gadolinium etc. is possible. Thus, the system can be adapted to specific analytical, therapeutic or diagnostic requirements.

If the interactive system is used for therapeutic or diagnostic purposes, it has to be made sure that the plastic material is physiologically acceptable, i.e. that it does not adversely interact with the physiological liquids. If the interactive system is used in the field of foodstuff, cosmetics or consumer goods, compatibility also has to be ensured. Furthermore, the interactive system can also be incorporated in suitable carriers, e.g. microsomes, liposomes, nanoparts, etc. in order to introduce it more easily into the organism.

Any desired substances can be coupled to the linker. The coupled substances may be the same or different. It is also possible to couple several different substances to different linkers. Preferably, pharmacologically or physiologically active substances are coupled to the linker. Examples thereof include proteins, nucleic acids, cellular signal substances, partners of a biological or physiological affinity pair such as for example DNA/DNA binding protein, DNA/complementary DNA, RNA/complementary RNA, antigen/antibody, streptavidin/biotin, strep-TAG/artificial peptide, lectin/carbohydrate or markers for a biological substance/ biological substance. More preferably, the protein is an enzyme, e.g. a lipase, an esterase, a transferase, an antigen, an antibody, a tumor marker, a surface antigen, a ligand, a receptor, a surface-active cell fragment of bacteria or viruses or an immune messenger substance, such as e.g. cytokines, interleukines, growth factors, colony-stimulating factors, tumor necrosis factors, apoptosis-inducing proteins or their specific antibodies or therapeutic agents. The marker is for example a fluorescent or chemilumenescent substance, an EST (Expression Sequence Tag) or an enzyme. The pharmacologically active substance is for example an anticoagulant, a metabolically active enzyme or a synthetic drug such as for example an antibiotic, an antitumor agent or an enzyme inhibitor. Additionally, substances can be coupled which react with inorganic ions such as for example nickel, zinc, gadolinium, lanthanum or gold. Examples thereof are the corresponding complexing agents. Substances coupled to a linker furthermore have the additional advantage that they can be eliminated from the organism.

Such an interactive system offers numerous possibilities of application. It is especially suitable for presenting substances coupled to the linker in a liquid, wherein the target substance is bound, cleaved or otherwise modified, or for eliminating substances coupled to the linker from a liquid. A preferred field of application is the monitoring of the diagnosis or therapy of metabolic diseases, coagulation defects, viral, bacterial, mycotic or parasitic infections or malignant diseases. Ready-to-use kits as well as devices in suitable housings and with the necessary equipment to operate the device can be manufactured from such interactive systems for specific applications.

Although the molecular principle of the interaction between the structural element (A) and the linker has not yet been examined, the following hypothetical binding mechanism is suggested, based on the interaction between polyalkylene glycol and polyalkyl(meth)acrylate which, however, should not restrict the present invention in any way. The carbonyl oxygen on the poly(meth)acrylate side chains has a strong negative charge due to the charge distribution in the hydrocarbon chain structure. Therefore, this oxygen can establish hydrogen bonds or electronic interactions with the polyalkylene glycol chain. The interactions can also involve the oxygen of the polyalkylene glycol which has a slight positive electron charge due to the —C—O—C configuration. An interaction between these two differently charged oxygen species in the poly(meth)acrylate and polyalkylene glycol is very likely so that the PEG chain is bound to the PMMA surface over a certain length of several C—C—O—C—C—O chain links.

In this connection, reference is made to the attached IR spectrum in FIG. 1. This figure shows the IR spectrum of polymethylmethacrylate, polyethylene glycol (5000) and PMMA-PEG interaction particles.

The illustration shows that a weighted addition of the PMMA and PEG spectra does not allow an identification of the individual spectra. What is especially remarkable is the decrease in intensity of the symmetrical $CH_2$ and $CH_3$ stretching vibration below 2900 $cm^{-1}$ compared to the free PMMA. This indicates that the adsorption of PEG and PMMA forced a certain new conformation. The most likely interactions of the PMMA and PEG interaction are the following:
1. ester group (PMMA) . . . H—O—H . . . ether (PEG)
2. ester group (PMMA) . . . H—C (methylene group, PEG)
3. carboxy group (PMMA) C—O—H . . . ether group (PEG) (few groups)
4. terminal group (PEG) C—O—H . . . ester group (PMMA).

The assignments all correspond to the OH stretching vibrations which occur in the PEG-PMMA complexes.

The found principle of the surprising bonding of the substance coupled to a linker with at least one structural element capable of establishing a hydrogen bond to surfaces with the structural element (A) allows different practical applications. On the one hand, such surfaces can be used as a functional antidote for certain active substances. On the other hand, such surfaces can easily be coated with coupled active substances and thus be used for example for in vivo blood purification or plasma treatment. It is, however, essential that this principle of interaction can be prepared separately (sterilization, sterile filtration and the like) and only be combined afterwards. These surface structures can be part of an extracorporal therapeutic system. Furthermore, by means of such a surface, coupled active substances can gently be removed from the organism after their reaction in the organism, preferably in the blood. Thus, for example dangerously high blood levels of PEG-hirudin can be antagonized, but also pegylated antibodies or pegylated protein active substances which were active in the blood for a limited period of time can be quantitatively removed (use of a reactive substance for a limited time). Moreover, for example PMMA capillary dialyzers can be locally anticoagulated by means of polyethylene glycol-coupled hirudin or other direct antithrombins (e.g. argatroban) (so that the patients require no systemic anticoagulant) but they can also be enabled to specifically interact with toxic or pathogenic or disease-promoting blood fractions or metabolites by coating capillary dialyzers with PEG antigens or PEG antibodies or PEG active substances.

Furthermore, the plastic material enabled to interact can also be part of surfaces of microtiter plates, cuvets or contact lenses. Additionally, it is also possible to use the linker as such without a coupled substance for saturating corresponding free bonds on the plastic material capable of interaction.

For a large number of medicaments, it would be advantageous if they had an effect only in the blood circulation. For this purpose, the molecular weight of the substances would have to be increased such that they cannot penetrate the fluid spaces outside of the blood vessels. However, the substances with an increased molecular weight cannot be used in applied medicine because it would then no longer be possible to eliminate these substances from the body via the renal output. The "renal threshold" lies in a molecular weight range below the size of the substances which prevents distribution outside of the blood circulation. Thus, the exclusive effect of substances in the blood circulation is an important problem which so far has not been solved. Only the possibility of fishing out PEG-coupled substances (prior art) within a defined molecular weight range with the help of e.g. polymethylmethacrylate surface structures makes it possible to use such medicaments in applied medicine.

The active surface preferably comprises a certain enlarged surface structure, e.g. pores, which can be formed by the manner the spinning process is carried out. For example, "foreign substance portions" are added to the heated polymer, e.g. glycerin, which are not miscible with the heated, liquid polymers. Drops or defects in the hollow fiber spinning result which are washed out of the membrane structure by means of suitable solvents, either water or organic solvents. Thus, the advantageous porous membranes are formed. In the case of micro- or macroparticles, which are suitable for another type of application, this porosity, the large "internal" surface of the particles, is formed in a similar manner. Here as well, dimensional structures are formed by the incorporation of foreign structures, e.g. glycerin; then the incorporated substances are removed by means of known spray or drop polymerization methods. The polymer structure is characteristically broken up and changed during this process. This porosity, the "internal structure" of the membranes or particles, is of essential importance for the binding of coupled substances.

The attached figures explain the invention in more detail.

FIG. 1 shows IR spectra of polymethylmethacrylate, polyethylene glycol (5000) and PMMA-PEG interactive particles.

Figure 2:
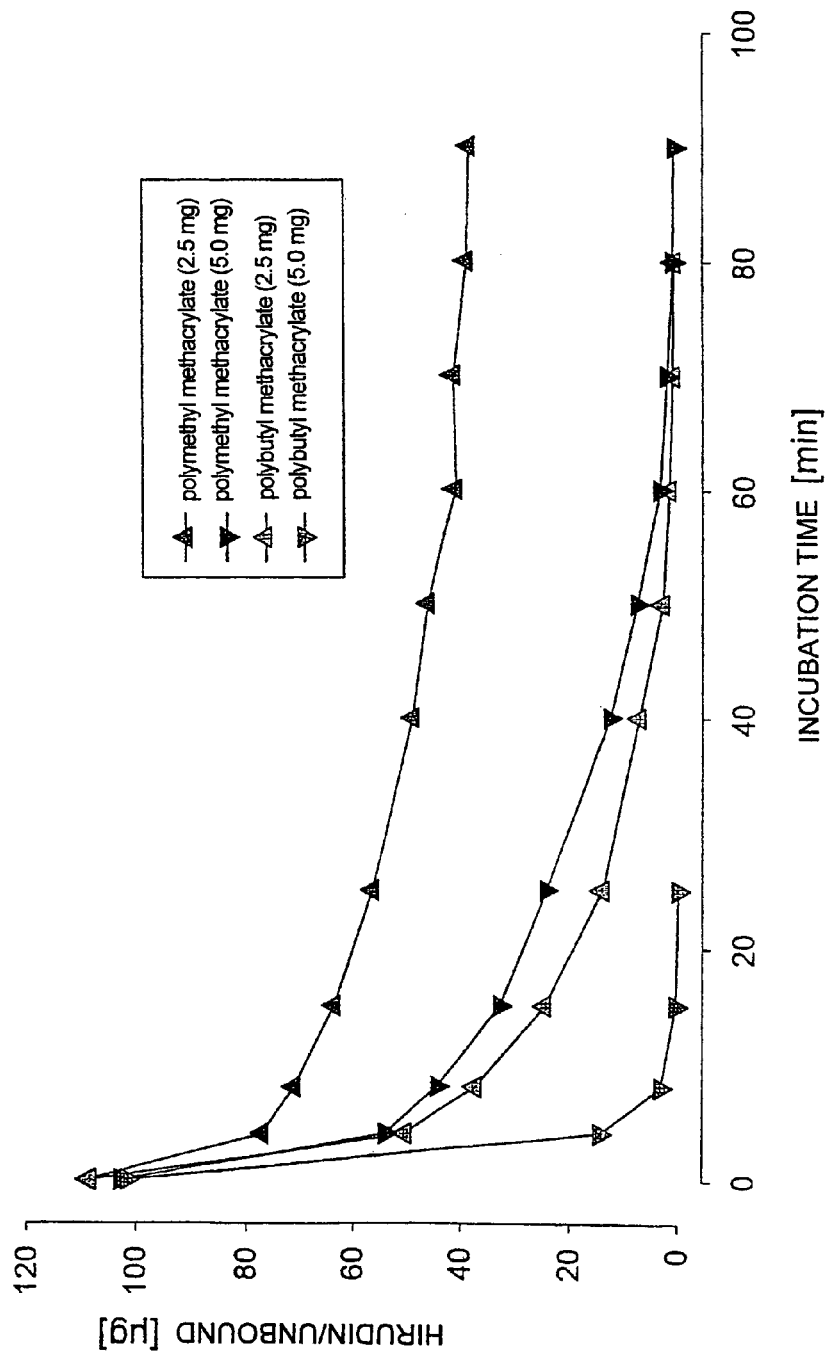
FIG. 2 is a representation of the binding of polyethylene glycol$_{10000}$-hirudin to microparticles from different polyalkylmethacrylates.

FIG. 2 shows the binding of polyethylene glycol$_{10000}$-hirudin to microparticles from different polyalkylmethacrylates.

Figure 3:
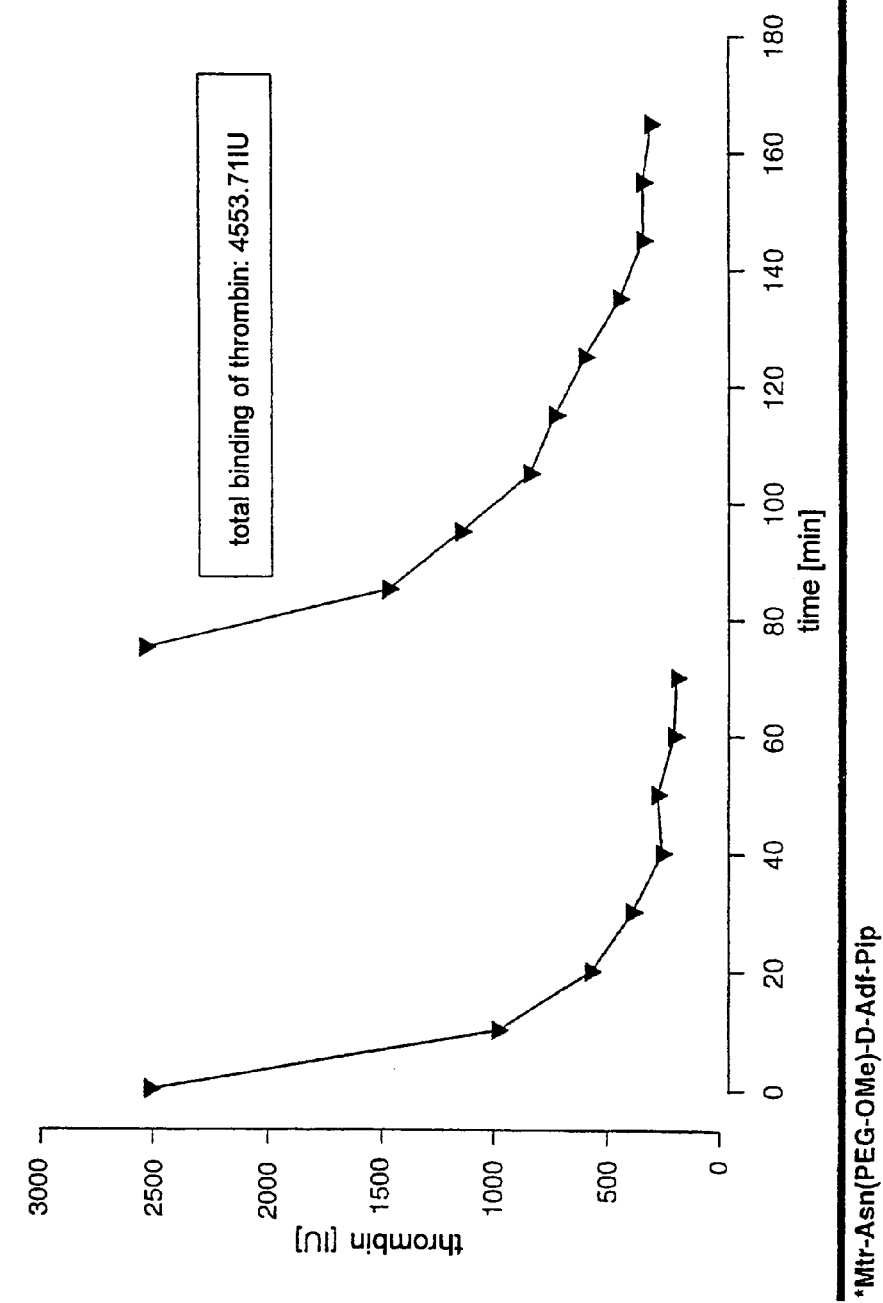
FIG. 3 is a representation of the binding of thrombin to a PMMA dialyzer loaded with synthetic PEG$_{10kD}$ thrombin inhibitor during repeated circulation of thrombin solutions.

FIG. 3 shows the binding of thrombin to a PMMA dialyzer loaded with synthetic PEG$_{10kD}$ thrombin inhibitor during repeated circulation of thrombin solutions.

Figure 4:
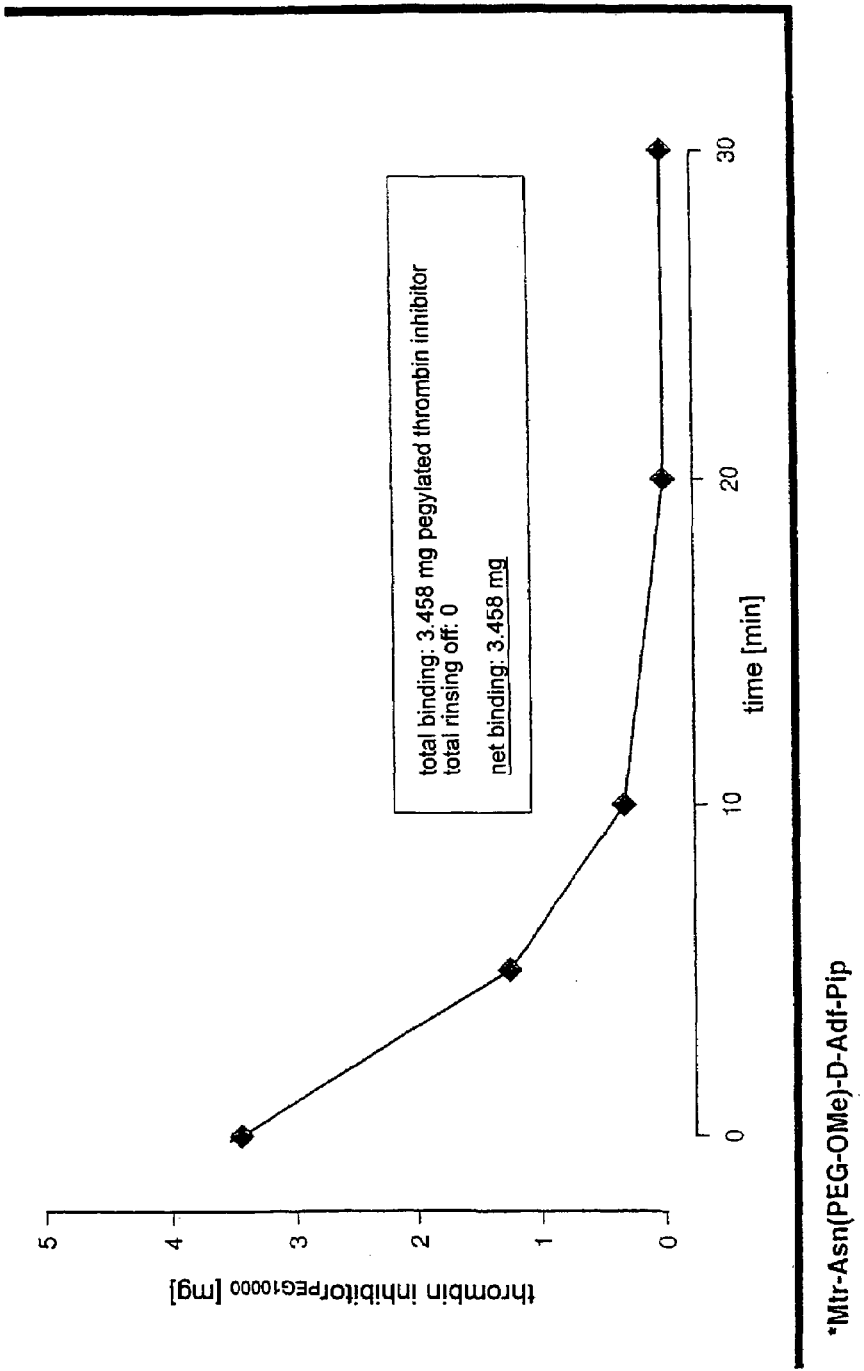
FIG. 4 is a representation of the binding of a synthetic PEG$_{10kD}$ thrombin inhibitor to a PMMA dialyzer during 30-minute circulations.

FIG. 4 shows the binding of a synthetic PEG10 kD thrombin inhibitor to a PMMA dialyzer during 30-minute circulations.

The invention is now explained in more detail on the basis of polyalkylene glycol-coupled active substances to poly(meth)acrylate surfaces.

1. Tube Systems

The commercially available polymethylmethacrylate dialyzers, e.g. from the company Toray, preferably high-flux systems, e.g. of the BK series, or low-flux dialyzers, e.g. of the B2 series, are opened at the two end portions and the capillary tube bundles (n=60) are isolated. After cutting three fiber bundles to a length of 12.7 cm, they are introduced into a polyethylene tube having a diameter of 1.4 cm. Silicone (A-Sil 2002) is pressed between the capillary dialyzer bundles extending about 0.5 cm out of the two open end portions such that the 8 to 10 mm thick casting material forms a completely tight seal of the open ends. After polymerization and curing of the casting material, the projecting capillary tubes are cut off flush with a sharp scalpel and the two tube system ends are each connected with polyethylene catheter material which allows flushing the capillary stretches by means of a pump. The systems are completely filled with salt solution such that there are no air bubbles. This way, these capillary tube systems can be stored at 4° C. and used for weeks.

2) Blood Filters

In polyethylene tube material with a diameter of 0.7 cm and stronger walls, slices of blood gas filter material from infusions systems are punched and the slices are adhered to the lower opening of 3 cm tube portions by means of a thermoplastic adhesive material. The cartridge is filled with porous PMMA particles in the preferred size between 80 and 120 µm and is then sealed at the top as well with the blood filter material. Then elastic silicone rubber tubes are attached tightly, connected to the material by means of thermoplastic adhesion and connected to support tubes. Using the same set-up, micro blood filters can be constructed consisting of 0.2 mm diameter PE tubes and having a length of 2 cm. The space to be filled with microparticles is then reduced to about one hundredth. Regarding their size and surface performance, these tube systems are also suitable for intravascular applications.

Prior to their application, the manufactured microcapillary or microcolumn modules can be sterilized by means of ETO or γ-rays. Steam sterilization is also possible for this material. The polyalkylene glycol-coupled active substances are only applied to the surface of the poly(meth)acrylate structure shortly before the system is used. This is done as follows: The poly(meth)acrylate carrier modules are rinsed with sterile physiological salt solution for about 10 minutes prior to the use in order to remove from the systems toxic products formed during the production or sterilization processes (standard technology in all external therapy systems such as hemodialyzers or oxygenators in medicine). After this cleaning process the substances to be applied, e.g. PEG-coupled substances, are applied onto the surface of the modules in a recirculation mode by priming the systems for 5 to 10 minutes with the PEG substance solution. Due to the high binding capacities, it is possible to apply several different PEG-coupled substances to the poly(meth)acrylate structure, either one after the other or a mixture thereof. In the experiments it could be unambiguously verified that there is no competition among the substances due to specific chemical structures relative to the surface of the poly(meth)acrylate. After conclusion of the priming process, the filters are again rinsed with salt solution for 1 to 2 minutes in order to remove residue of PEG substances from the system which had not been completely bound. Then the external therapeutic system is connected by means of the conventional one- or two-needle technology venovenously or arteriovenously. The venovenous passive application has the advantage that the blood circulation through the system can be controlled by means of the miniature blood pumps which are introduced into the extracorporal circulation. The effectivity of the specific substrate "fishing" is determined by examining the disappearance of the target pathogens. Corresponding detection methods exist for almost all the used active substances.

The kits of the external therapeutic systems offer a selection of various sizes of blood filters so that they can be adjusted to the necessary amount of primed substance. For this purpose, a conversion chart exists which is known from pre-clinical tests of such systems. According to a sort of "modular assembly concept", the physician can choose from a reservoir of different pegylated active substances and different blood filters and put together individual therapeutic packages suitable for his patient in view of the therapeutic agents and the size of the system. Such kits optionally contain suitable reagents, buffer solutions, reaction vessels and the like. The kit can also be present in suitable packaging.

Analogously, such application kits can also be assembled as biochemical purification systems. The module size is adjusted to the corresponding preparative application. For biochemical preparative problems and for in vitro testing, not only the column system but also the batch system can be used. The corresponding micro- or macroparticles are intimately mixed in a batch volume and after priming with the polyalkylated substances and centrifugation of the supernatant, the loaded particles are again twice washed with salt solution and then the suitable preparation solution is added. By fishing out the "appropriate" reactants, the antigens and antibodies or chemically interactive substances can be separated. This allows e.g. a preparative affinity purification with an efficiency of almost 100%.

An exemplary list of possible applications of the above-mentioned systems is given below.

A) Eliminating Substances From the Blood:

1. For using specific antigen-antibody reactions, the present monoclonal or polyclonal antibodies are coupled with polyethylene glycol and these PEG antibodies are then applied to the PMMA surface. As specific a recognition of the epitopes of the substance to be eliminated as possible is extremely important for a rapid and strong bonding to the prepared surface. According to the method described above, the PEG antibodies are primed to the blood filter of the selected size, and by adding a pegylated antithrombin, e.g. PEG hirudin, a local anticoagulation of the systems is aimed at. The predominant advantage of the local anticoagulant effect with the help of pegylated antithrombins is that the patient to be treated does not need to be anticoagulated systemically during the treatment with the external therapeutic systems.

2. For the treatment of inhibitor hemophilia, a serious autoimmune disease, human factor VIII (antihemophilic globulin) is coupled to polyethylene glycol using known methods and then primed onto a polyalkylacrylate substrate of a suitable size. The inhibitor-hemophilia modules produced in this manner are used at regular intervals as external therapeutic system for affected patients. The intervals of this treatment depend on the measurable "consumption" of factor VIII in the patient. The factor VIII level should not fall below 25 to 30% of the normal value. Between the treatment intervals, the patients are in no danger of bleeding or hemorrhagic diathesis so that this form of therapy can be called a causal treatment.

3. Antimicrobial treatment possibilities: The methods of molecular medicine make it possible to produce monoclonal or polyclonal antibodies against almost all viruses having protein-containing envelopes, against bacteria but also against fungi. These antibodies directed against microbe-specific proteins can be primed onto the substance substrates made from polyalkylacrylate after they have been coupled with polyethylene glycol of a suitable size (preferably 5-10 kDa). By treating patients with such external therapeutic systems, it is possible to eliminate pathogenic or disease-promoting and -maintaining germs from the bloodstream. Specifically, this method is excellently suitable to treat for example malaria. The cyclic use of specific substrates carrying active substances makes it possible to interrupt the disease and to achieve a rapid recovery of the patient.

4. Preparation of locally anticoagulative hemodialysis and hemofiltration systems: When polymethylmethacrylate hemodialysis apparatuses or hemofiltration modules (products of the company Toray, Japan) are used, the modules are treated with polyethylene glycol hirudin solution after rinsing of the systems and prior to their use. By recirculating PEG-hirudin, an anticoagulant effect is achieved at the membrane surface. Depending on the duration of the treatment, the systems have to be treated with varying amounts of PEG-hirudin (5-50 mg).

5. Preparation of locally anticoagulant blood tube systems: By using conventional blood tube systems (PS, PE, PP and the like), during the manufacture of which at least 20%, more preferably 50%, of polyalkylmethacrylates, preferably polybutylmethacrylate, has been added, priming with PEG-hirudin or PEG-coupled synthetic thrombin inhibitors is possible. Thus, a local anticoagulation extending to all the blood tube systems, both of the arterial and the venous type, is also possible.

B) Applying Enzymes which Influence Certain Constituents of the Blood or Proteins:

This applies for example to the following substances: 1. enzymes which are involved directly or indirectly in the body's control mechanisms, e.g. which activate or inhibit specific blood-clotting factors. By PEG-coupling of e.g. protac, a snake poison enzyme which activates protein C in a highly specific manner, a whole new long-term thrombosis prophylaxis without hemorrhagic diathesis or other side effects in the sense of the therapeutic substances used so far presents itself. The enzyme protac activates protein C into protein $C_A$ which interferes with blood clotting by inhibiting the activated factors V and VII. Both factors are activated by thrombin and have a positive feedback effect on the thrombin activation itself so that a potentiation cycle results which can immediately be interrupted by inhibiting these two acceleration factors (clinical equivalents are protein C deficiencies accompanied by serious thromboembolic diseases). But also blood sugar level regulating enzymes such as glucose-dehydrogenase and other enzymes can regulate pathological or pathophysiological changes in the sense of a metabolic disease in the bloodstream (hypercholesterolemia, hyperlipidemia, diabetes mellitus type II or certain storage diseases). Influencing endocrinologic metabolic disorders is a possible form of application.

C) Applying Substances Significant for Vital Functions

1) Artificial Blood

There is also the possibility to provide artificial erythrocytes. A PEG hemoglobin, for example extracted from bovine blood, is currently being clinically tested as "artificial blood component" ("oxyglobin"). PEG hemoglobins should be applied to suitable paramagnetic polymethylmethacrylate or polyalkylmethacrylate particles, which have been graded according to size, and then used accordingly. Ideally, the particles have the same specific weight as blood. Thus, polyalkylmethacrylate polystyrene copolymers in a 50/50 mixing ratio, more preferably in a 30/70 mixing ratio, are used. For this, for example 1 g monodisperse, porous polymethylmethacrylate particles (or PMMA polystyrene) (d=6 µm) are primed with 250 mg PEG-coupled hemoglobin (for example experimental preparation from the company Enzon). The indication of weight relates to the hemoglobin portion. The polymethylmethacrylate particles (PMMA polystyrene) have been specifically prepared by introducing $Fe_2O_3$ in finely dispersed form into the polymerization mass during polymerization. These $Fe_2O_3$-containing particles are paramagnetic and can be removed from the circulation in the above-mentioned way.

Such magnetically active particles are suitable for a direct circulative use in blood in manifold ways. Apart from the above-described PEG hemoglobin, NO donors (specific inhibition of the blood platelet activation) but also specific interaction partners for cells, preferably tumorous cells, can be coupled. In the treatment of tumors, a "fixation" of the particles carrying the anti-tumour active ingredient can be realized by way of magnetic fields in the tumour area.

The hemoglobin particles have a high oxygen binding function and can assume the oxygen transport function in the entire blood circulation similar to the function of the erythrocytes. Thus, these hemoglobin microparticles are suitable as universal oxygen carrier system in disaster medicine.

It is of particular importance that the oxygen transport as the most important disordered vital function after a massive blood loss be reestablished very fast. At the end of the treatment lasting for several days, when the organism concerned has resynthesized the respective corpuscles, the particles can be quantitatively removed from the circulation by way of magnetic retention systems. These magnetic retention systems are for example microcapillary ETS which are surrounded by a permanent magnetic ring. The magnetic particles are removed from the circulation by attachment to the hollow fibers of the ETS.

2) Cell Growth-Stimulating Factors

The described basic principle of the attachment of active ingredients to specific polymer materials is also suitable for coating other plastic surfaces, cell separators or cell cultivation materials wherein an increased growth impulse is achieved by pasting thin layers of very fine microparticles from PMMA, thus enabling an application of cell growth factors (for example pegylated BMP-2 or BMP-4). This can also be used in order to coat vascular prostheses with growth factors in such a way that endothelial cells settle very rapidly and intensively on the blood side of the vascular prostheses initiating a naturalization ("endothelialization") of the vascular prosthesis there. By the specific doping of the tissue side of the prostheses for the purpose of ingrowth of connective tissue cells and smooth muscle cells, for example by applying basic fibroblast growth factor (bFGF), even a naturalization of the entire prosthetic material is possible. The coating of arthroplastic material with pegylated rBMP-2 or rBMP-4, two recombinantly prepared osteoblast growth factors, or the admixture of porous microparticles from PAMA with rBMP-2 or rBMP-4 in bone cements enormously reduces the ingrowth phase. Thus, considerably improved fixation results are achieved.

D) Separation techniques of microparticles for viruses and bacteria and their metabolic products in blood and plasma donations.

By treating the plasma with specific PMMA-PEG-antibodies against envelope proteins or virus DNA, it is possible to purify human plasma samples in a very gentle way. Especially in viruses having specific proteins (hepatitis B virus protein E1 and E2, AIDS virus proteins), a quantitative removal is possible. This can be carried out both in the batch and in the column processes.

E) Use of PMMA-PEG-particles for removing undesired substances from food, for example for dealcoholizing alcoholic drinks such as beer, wine etc., presentation of special lipases or enzymes which decompose excessive dietary fats into non-absorptive derivatives or bond suitable compounds to their surface, removal of cholesterol, selective removal of certain protein components in certain metabolic disorders (for example gluten in cases of coeliac disease), removal of certain carbohydrates in cases of diabetes etc.)

On this basis, design food and dietary products can be prepared for specific diet requirements by adding suitably coated microparticles according to the invention to the product or by suitably pretreating the product. It is also possible to take suitable microparticles before, during, and after the consumption of the respective food. For this purpose, the microparticles can be formulated as gastric and intestinal juice resistant tablets or capsules.

F) Installation of micro blood filters in the blood stream by means of the so-called vein "filter" technique as is currently being employed by invasive radiology in deep leg and pelvic venous thromboses. A so-called cava filter in the form of a wire cage, is stretched out and installed in the vena cava in order to prevent considerable thrombotic masses from being elutriated into the lung flow. This cava filter technique might also be used as fixing or carrier material for micro blood filters. The same coating materials as described above are used. However, such a system should then rather have the form of a flat blood filter having an interfacial area as huge as possible.

G) Oral Application of Particular Carriers of Active Ingredients:

There are two different possibilities:

1) Substitution of Disordered Digestive Functions:

Similar to the delivery systems for digestive enzymes still in the development stage, certain particles according to the invention containing a permanent digestive enzyme coating can be used. These particles can assume essential digestive functions during their passage through the gastrointestinal canal. A permanent instillation of digestion-promoting intestinal tubes is possible if, in a suitable fibrillary or similar structure, the enzymes in the small intestine are used on a certain polyalkylacrylate matrix. A permanent indwelling gastric tube in the form of a structured plastic cage is for example equipped with filamentary PMMA structures to which the enzymes are permanently bonded via the PMMA-PEG coupling over a distance of 30-50 cm. They pass into the small intestine together with the food mash and at one end still have firm contact with the stomach fixation. The respective enzymes can imitate the digestive function in the gastrointestinal canal over a quite long period of time. They start acting when respective food components pass the fibrillary structures.

2) Corpuscular or particular enzyme carriers metabolizing special portions or specific food components with the aim to be changed into a chemical derivative which is not resorptive anymore. For this, plant enzymes which are able to modify cholesterol and other food compounds rich in fat and energy are suitable. Binding cholesterol and fat-resorbing bile acids to suitable binding partners on the surface of these gastrointestinal particles is also a possible method. For specific application, also particles according to the invention having a high concentration of alcohol dehydrogenase are suitable to decompose undesired amounts of alcohol already in the gastrointestinal canal.

A specific application is for example the use of pegylated monoclonal antibodies against the tumor necrosis factor (TNF). The monoclonal antibody against the tumor necrosis factor (MAK-195) is a test preparation from the company Knoll and is currently being evaluated in clinical studies with shock patients as to its clinical efficiency. This monoclonal antibody can be coupled with PEG and applied to a suitable PMMA structure without any problems. Thus, the monoclonal antibody is solid phase bound and highly specifically binds an epitope of the tumor necrosis factor. Thus, high TNF levels which are pathophysiologically detrimental to the further course of a shock reaction can be reduced. Similarly, monoclonal or polyclonal antibodies against lipopolysaccharide-binding protein (LBP) can be coupled. This protein serves the transport of bacterial metabolic products of the lipopolysaccharides (endotoxins, lipid A) in the blood and their presentation to the cells. If the level of liposaccharide binding protein is reduced, the insorption of endotoxins from the gastrointestinal canal but also from sources of inflammation can thus be completely blocked.

Furthermore, it is for example also possible to pegylate specific human γ-globulin fractions and to coat them on the PMMA membrane in order to directly inhibit bacteria or viruses and to remove them from the organism via the temporary extracorporal therapeutic system.

Furthermore, also inhibitors for activated coagulation factors, for example the recombinant TFPI, a natural inhibitor of the factor VII-tissue factor complex, the most important starting mechanism of blood coagulation, can be used. In suitably pegylated form, they can be bonded to the membrane in order to completely inhibit blood coagulation in the first activating mechanisms without influencing the normal coagulation potential of the organism. In principle, any pathological mechanism of the organism using the blood stream for signal transmission, can be modified by such an extracorporal therapeutic system.

The bondability of such surface doped capillary dialyzers is surprisingly high; up to 1 g pegylated structures can be bonded on 1 m² surface. Washing-out attempts doubtlessly demonstrated that the physicochemically explainable connection between the pegylated active ingredient and the PAMA membrane is very stable and a disconnection from the membrane both by rinsing with salt and by rinsing with plasma or whole blood is not possible.

From molecular immunology, a number of specific tumor antigens at cell surfaces of tumor cells are known, for which suitable antibodies for in-vitro examination are available for diagnostic purposes. However, their foreign protein structures do not allow an application in patients. According to the invention, these antibodies, bound to PEG linkers at the surface of a PMMA membrane, can form a specific interaction with tumor cells of the blood and specifically remove them from the circulation similar to hemofiltration. Thus, this is the first time that a system has been provided wherein on the basis of present surface material, which is biocompatible and approved, a specific interaction in the blood between cells or cell parts of the organism and solid phase bonded specific antagonists is possible.

The interactive systems according to the invention can be applied in many other therapeutic applications, particularly to the in vivo plasma purification. For example, ultrafiltration membranes of the PMMA type, to which special PEG-coupled enzymes have been applied, can be employed for detoxication in patients with a renal disorder. Furthermore, by applying PEG-coupled urease to PMMA membranes, elevated urea levels in the blood can be lowered, or, by applying PEG-coupled creatinine metabolizing enzymes, a reduction of further, nitrogen usually eliminated with the urine can be achieved.

The use of the interactive systems according to the invention, preferably of PMMA membranes in capillary dialyzers is preferred. The sole manufacturer of PMMA capillary dialyzers is the company Toray, Japan. Prior to their application in human patients, the capillary dialyzer modules are thoroughly rinsed both on the dialysate side and the blood side, on the blood side with physiological sodium chloride solution, on the dialysate side with dialysate liquid (salt solution) in order to wash toxic products and substances which have gotten into contact with the system during the production process, out of the capillary dialyzer. At the end of this continuous rinsing process, wherein the rinsing liquid is discarded on both sides, the dialysate side is capped with a stopper in preparation of the external therapeutic system on the blood side, a recirculation is attached with the pegylated substance to be applied being dissolved in the solution reservoir of about 200 ml. By way of a simple recyclization process wherein at the exit of the dialyzer the solution is pumped back into the solution reservoir via a peristaltic pump, the membrane is coated within 5-10 min with the pegylated substance. Independently of their cutoff (dimension figure of the pore size in the membrane) the membranes accept up to 200 mg of the substance to be coated on (=1 g of the pegylated active substance) per m² of capillary surface. It is important that the relevant binding sites on the PMMA membrane are completely occupied by the pegylated active substance. If only small amounts of these active substances are applied, an additional rinsing step with PEG salt solution should be carried out at the end of the rinsing process in order to saturate all PEG binding sites of the membrane. Thus it is guaranteed that an additional coating with plasma proteins of the blood does not occur at the binding sites anymore and thus no interaction between plasma proteins and the presented active substances takes place (priming).

In the following, the invention will be described in more detail on the basis of the following examples.

EXAMPLE 1

Use of Polyethylene Glycol Coupled Hirudin in Dialysis

In its recombinant, nature identical form, hirudin is a highly specific and effective antithrombotic principle which will gain increasing attention with regard to the sufficient therapy of thromboembolic diseases and their resulting conditions in the next few years.

The effectivity of this new, therapeutically valuable substance has been proven by first clinical applications and extensive phase-III studies.

Recombinant hirudin can of course lead to intoxications, either by the type of the therapeutic scheme carried out, by overdosage or by objective elimination difficulties which occur due to sudden or transitory kidney insufficiencies.

For removing hirudin from the organism there are currently two ways in clinical medicine, i.e. the application of an antidote (see German patent specifications P 42 03 965.7 and 196 25 642.9, and EP 0 625 908) as well as the fast removal of the hirudin by means of high-flux dialysis membranes.

In clinical practice, particularly a hirudin derivative of high molecular weight has turned out to be suitable for practical application. It is a hirudin wherein the molecular weight is increased by two 5000-D-polyethylene glycol chains. After application, an up to 4-5 times higher amount of substance in the organism and a considerably extended plasma detention time of the hirudin is achieved.

Antagonizing this PEG hirudin in case of overdosage or toxic blood levels turns out to be difficult. Although the universal antidote principle against hirudins and against synthetic thrombin inhibitors as described above can also be used for PEG hirudin, but a general dialysability of PEG hirudin does not exist. PEG hirudin does not even pass hemofiltration systems having an extremely high cutoff. Accordingly, a quickly available functional antidote formulation is not possible so far.

Upon comparison of hirudin and PEG molecular weight increased hirudin in corresponding in vitro but also in vivo circulations through PMMA capillary dialyzers and PMMA hemofilters, a completely different behavior was observed. While native or recombinant hirudin passes very quickly from the blood side to the dialysate side and then disappears from the circulation, PEG hirudin behaves in a completely different way. It was demonstrated that in a capillary dialyzer recirculation model, after a short period of time there is no PEG hirudin in free form anymore both on the blood and on the dialysate side although relatively high amounts of PEG hirudin on the blood side were either applied in anticoagulated bovine blood or also in protein salt solution. Thus, it was demonstrated that in this recirculation model PEG hirudin from whole blood, plasma or albumin recirculation solution is strongly bound at high rates on the PMMA membrane surface. An attempt to achieve a bleeding off or washing out of the PEG hirudin from the membrane after removing the examined circulation solution by means of salt solutions failed; the bond turned out to be quite stable and strong.

From these analyses it is clear that a functional antidote principle for PEG hirudin is possible. Such dialyzers can thus be used in different ways:

For example, a PMMA dialyzer can be connected to a normal dialyzer and be used as functional antidote principle for PEG hirudin in corresponding clinical applications, or the PMMA dialyzers can be operated by simple hemofiltration pumping systems, as used in intensive medicine for continuous hemoperfusion (see example), with the dialysate side being capped so that a relatively unproblematic hemodialysis with low volume load can be carried out in the patient concerned. The time required for the hemodialysis, even in case of high concentrations of PEG hirudin in the blood, would in these cases be less than 2 h, preferably 30-45 min.

For extracorporal therapy of the blood by means of effective dialysis of metabolic products usually eliminated with the urine, membrane materials having as high a biocompatibility as possible and having constant filter performance over a long period of time are being developed. Polymethylmethacrylate (PMMA) offers an excellent clearance of average molecules and ultrafiltration performances which can be exactly controlled via the transmembrane pressure.

EXAMPLE 2

Preparation of PEG-Modified Hirudin Goat Antibodies

1) Preparation of SC-PEG
Method according to T. Miron and M. Wilchek (literature: Bioconjugate Chem. 1993, 4, 568-569)

Materials

| | |
|---|---|
| acetone | water-free |
| diethylether | water-free |
| 1,4-dioxane | water-free |
| molecular sieve | 4A, beads 8-12 mesh |
| phosphate buffer | 0.05 mol/l; pH 7.0 |
| polyethylene glycol 6000 | MW 5000-7000; 1 mmol |
| N,N'-disuccineimidylcarbonate | 5 mmol |
| 4-(dimethylamino)pyridine | 5 mmol |

Procedure:
1 mmol PEG is dissolved in 25 ml water-free dioxane (via a molecular sieve) in a hot water bath. After cooling to room temperature, the N,N'-disuccineimidylcarbonate, dissolved in 10 ml acetone, is added. Subsequently, the 10 ml acetone, together with 5 mmol 4-(dimethylamino)pyridine, are slowly added under stirring. At room temperature, the mixture is activated for 6 hours (magnetic stirrer). The activated PEG is directly precipitated from this solution by diethylether. The voluminous white precipitate is drawn off by means of a G3 frit. The complete removal of the ether is carried out in the evacuated exsiccator. Storage: dry at 4° C. Efficiency: 85% (based on PEG)

2) Coupling of SC-PEG with Protein a) Preparation of PEG Modified Hirudin:

Materials: borate buffer, pH 9.5
phosphate buffer, pH 7.0; 0.05 mol/l
hirudin; recombinant
SC-PEG Procedure:
150 mg PEG and 27 mg hirudin were dissolved together in 25 ml borate buffer and incubated under stirring for 3 hours at 4° C. Unbound PEG and hirudin are removed by ultrafiltration (AMICON; membrane YM 10) with the 6 to 10-fold volume of phosphate buffer. The remainder is lyophilized and stored in the exsiccator at 4° C. The individual preparation steps are verified by SDS-PAGE, coagulation tests (ECT), PEG determination and animal experiments.

b) Preparation of PEG-Modified Hirudin ZAK (Goat Antibody):

Materials: phosphate buffer pH 7.0; 0.05 mol/l
SC-PEG
hirudin goat antibody (Hi-ZAK)

Procedure:
500 mg PEG are dissolved in 20 ml Hi-ZAK (present in phosphate buffer) and incubated for 48 hours at 4° C. under stirring. Free PEG and Hi-ZAK are removed by ultrafiltration (AMICON; membrane YM 10) with the 6 to 10-fold volume of phosphate buffer. The preparation was stored as solution at 4° C.

These PEG-modified hirudin goat antibodies can be applied to a PMMA membrane and thus, if used in an extracorporal therapeutic system, high hirudin levels in the blood can be reduced.

EXAMPLE 3

"Removal" of PEG Hirudin from Blood

In the following experimental example, the efficiency of the removal of PEG hirudin from the blood is to be demonstrated. For this purpose, 250 or 300 ml whole bovine blood are anticoagulated with 36 µg/ml PEG hirudin and introduced into PMMA dialysis recirculation systems prepared accordingly and available for the application. For this recirculation model, the following experimental set-up is employed:

A hemodialysis unit of the Fresenius A2008C type is used for pre-rinsing the blood and dialysate sides of the dialyzers. The PMMA dialyzers are prepared for dialysis according to the specifications of the manufacturer. At the end of the pre-rinsing of the PMMA dialysis membrane, the inlet and outlet of the dialysate side is completely closed with hose clips so that the dialysis solution cannot be changed during the experiment. The hose pump of the dialysis unit is connected to a storage container and to the arteriovenous side. The extracted and PEG hirudin anticoagulated bovine blood is filled into the siliconized glass storage container and the recirculation of the blood side is started immediately. Within short intervals, samples are taken from the blood reservoir and the hirudin concentration in the recirculation system is measured on the basis of the Ecarin clotting time (see German patent application P 42 03 965.7). As can be taken from FIG. 3, a quick drop of the hirudin concentration in the blood occurs upon the beginning of the circulation of the PMMA membrane, i.e. within the first 40 minutes.

FIG. 3 shows the surface bond of a synthetic, thrombin inhibitor of small molecular size prepared with polyethylene glycol (10 kD) according to the specification of W. Stüber et al. (Peptide Research 8 (2) 1995, pages 78-85) as pegylated inhibiting agent. The effective thrombin inhibitor principle is the substance Mtr-Asn-D-Adf-Pip which has turned out to be a highly specific and effective thrombin inhibiting agent in previous analyses (Dickneite G. et al. Thrombosis Research 77, pages 537-568).

FIG. 4 shows the binding of thrombin to a PMMA dialyzer charged with PEG-(10 kD)-thrombin inhibitor. From this figure it is obvious that thrombin binds to the coupled thrombin inhibitor during recirculation and thus quickly disappears from the recirculation solution.

From the PEG hirudin concentrations on the blood and dialysate sides described here, it is obvious that on both sides of the recirculation system, no measurable PEG hirudin is present anymore.

For comparative purposes, the behavior of recombinant hirudin when PMMA dialyzers are used is shown. The blood used was bovine blood which had been anticoagulated with 30-50 µg/ml r-hirudin. From the figure it is apparent that a reduction of the hirudin concentration also occurs on the blood side, which, however, quickly becomes steady-state. The examination after the two-hour hemodialysis showed high concentrations of r-hirudin in the dialysate side similar to those on the blood side, i.e. there is a typical total r-hirudin concentration equilibrium on both sides. The adsorptive binding (loss of r-hirudin) is so small that it can be neglected. From the analyses presented here it is obvious that PEG hirudin having high specificity is bound to PMMA capillary dialyzers. The direct comparison with the unbound r-hirudin doubtlessly allows the conclusion that the PEG portion of the hirudin is responsible for the coupling on the PMMA surface.

EXAMPLE 4

Preparation and use of a Polyethylene Glycol (20000) Coupled Monoclonal Antibody Against Tumor Necrosis Factor (MAK 195)

100 mg MAK 195 are dissolved in 50 ml of 0.1-mol borate buffer (pH 8) and added to 200 mg methoxy polyethylene glycol (20000)-4-nitrophenyl carbonate and then incubated for 3 h at 25° C. The coupling reaction is stopped by means of a 500-fold molar excess of TRIS, dialyzed against 20 mmol TRIS-HCl and applied to a HP-Q-sepharose column (Pharmacia) with a linear NaCl gradient (of 0-400 mmol NaCl) in 20 mmol TRIS-HCl (pH 8). The PEG-MAK 195 conjugate elutes at about 200-250 mmol NaCl. The binding ability of the monoclonal antibody is tested on the basis of a recombinant human α-TNF by means of an α-TNF-ELISA. A loss in effectivity of the monoclonal antibody cannot be observed. The pegylated monoclonal antibody against TNF is applied to an experimental PMMA capillary dialyzer module having a surface of 50 cm$^2$. The bondability for 50 cm$^2$ surface was 4 mg, based on the protein content of the PEG-MAK 195. In human plasma, which was spiked with TNF (100 ng/ml), no tumor necrosis factor could be identified in the recirculation solution anymore after only 10 minutes.

A further series of experiments was carried out wherein 50 ml human blood was added to PEG-MAK 195 in a concentration of 1 mg per ml. This PEG-MAK blood amount was added to an experimental PMMA capillary dialyzer having a surface of 50 cm$^2$ by way of recirculation and recycled by way of a hose pump. After 30 min of perfusion, no MAK-antibody could be identified in the concerned blood anymore. The identification was carried out by means of a TNF inhibitory assay on the measuring basis of a TNF-ELISA. These two experiments doubtlessly prove that the pegylated monoclonal antibody, in the present case the TNF antibody MAK 195 (Knoll), can be specifically coated on the PMMA capillary dialyzer membrane where it is able to quantitatively bind human TNFα.

In the second experiment it was demonstrated that a pegylated monoclonal antibody present in the blood is specifically removed from the circulation by the PMMA membrane. This experiment demonstrates the "fishing" of a pegylated active ingredient employed in the blood for a limited period of time.

EXAMPLE 5

Use of a PEG-Coupled Enzyme

As model enzyme, urease (EC 3.5.1.5., available from Sigma, order no. U 1500) is used. The preparation of a PEG-coupled urease preparation: 100 mg urease (type III, specific activity 20,000 to 30,000 U/g) are dissolved in 80 ml 0.1-mol borate buffer (pH 8) and added to 250 mg methoxy polyethylene glycol (25,000)-4-nitrophenyl carbonate and incubated for 24 h at 5° C. The reaction is stopped by a several times higher molar excess of TRIS, dialyzed against TRIS-HCl (pH 8) and developed in a HP-Q-sepharose column having a linear NaCl gradient (pH 8). The PEG urease conjugate elutes-at 180 to 200 mmol NaCl. The yield of PEG urease conjugate is 30-40%. The enzyme activity is measured by means of a urea assay. The cleaving activity is monitored by way of pH titration measuring and compared with non-conjugated urease. The pegylation of the urease has a slightly activity-increasing influence on the ureolytic activity of the enzyme. The urease coupled with 25 kD-polyethylene glycol is applied in a concentration of 2 mg (based on the protein content of the conjugate) to a miniaturized experimental capillary dialyzer having a surface of 50 cm$^2$. Already after the first circulation, more than 90% of the urease are immobilized on the surface. By the fifth recirculation cycle, the PEG urease is firmly installed on the surface of the membrane. A washing out by rinsing for 30 min with an albumin-salt solution did not result in an activity loss or the occurrence of free urease activity in the rinsing liquid. A blood plasma solution (50 ml containing 30 mg urea) is applied to the urease-doped PMMA capillary dialyzer system. In the eluate of the experimental PEG-urease-PMMA membrane, the remaining amounts of urea are identified after 5, 10, 20, and 30 minutes by way of an enzyme assay. It can be shown that the urea concentration in the blood plasma decreases rapidly within the first 10 min. After 30 min, unbound urea cannot be identified anymore. The ammonia test in the blood is positive during the last 25 minutes of the experiment. From the analysis, it can be doubtlessly concluded that a pegylated enzyme, bonded to the PMMA membrane, develops a local enzyme activity and is able to generate corresponding specific interactions with its substrate in the circulating blood.

EXAMPLE 6

Preparation and use of Polyalkylmethacrylate Microparticles

In further experiments it could be verified that microparticles of polyalkylmethacrylate (PAMA) are also able to bind these polyethylene glycol-coupled substances on their surface. The PAMA microparticles are prepared according to known methods and coated with the respective active substances. Different particle sizes were examined. Microparticles of polyalkylmethacrylate with a diameter between 0.5 and 250 µm bind large amounts of PEG active substances. These particles can be used in many ways:

1) Particles having a Diameter of up to 20 µm:

After specific PEG active substance doping, these particles can be applied by the intravascular route and then remain in the bloodstream for a longer period of time. There is the possibility of channeling these particles out of the body again if they contain compounds which are magnetically excitable (e.g. $Fe_2O_3$). By means of a specific external treatment of the blood with magnetic retention systems these particle can be removed from the bloodstream at the end of the therapy. Here, prodrugs (substances which are only converted to their effective form by enzymes present in the blood) could e.g. be transported to certain organs or the focus of a disease in the organism where they are then present for therapy in high concentrations.

1.1 Oxygen Transport Vehicles

By priming these PAMA particles with polyethylene glycol-coupled hemoglobin, "artificial" erythrocytes are formed which have a high specific oxygen transport capability and sufficiently long retention time in the organism.

1.2 Antiviral Particles

Specific polyclonal or monoclonal antibodies against coat proteins (highly specific recognition points) of the viruses are primed onto the PAMA particles. The particles are able to quantitatively "catch" the viruses and remove them from the organism.

1.3 Particles Carrying Monoclonal Antibodies (MAB)

MAB particles against tumor necrosis factor (TNF-α) can be used both against sepsis and in serious infectious diseases. The MAB particles "find" the TNF-α produced by the infected cells, which in some infectious diseases is also released in high concentrations after contact with endotoxin.

1.4 Particle-Coated Solid Bodies and Tissue 1.4.1 Material for Arthroplasties or Vascular Prostheses Monodisperse particles of the preferred size 1 µm, 5 µm or 10 µm are strongly adhered to the prosthesis material by means of a suitable adhesive film ("PAMA adhesive"). After curing of the adhesive bond, the materials coated with PAMA particles are primed with polyalkyl glycol-coupled growth factors for bone, connective tissue or muscle cells (e.g. rBMP-2 or rBMP-4, bFGF etc.) and then introduced into the body. This allows for the first time to achieve a strong connection between prosthesis material and the muscle (reconstructive traumatology!).

1.4.2 Vascular Prostheses

A PAMA particle (diameter 0.5 µm) layer is applied to Goretex or Dacron vascular prostheses and prior to their use they are primed with pegylated endothelial growth factor. The additional application of basic fibroblastic growth factor, which had been PEG-coupled, enables an improved vitalization by means of growth induction in connective tissue and microcapillaries.

1.4.3 Artificial Organs

Biocompatible tissue layers made from plastic materials onto which monodisperse PAMA particles had been adhered or copolymers having PAMA as a basic material are primed with organ-specific pegylated cellular growth factor. This allows a rapid and controlled coating of the organ substitute materials.

Fields of application: liver substitute, bone marrow substitute, lung tissue substitute etc.

1.4.4 Cell-Chip Contacts

Biosensors, such as e.g. silicon chips and other electronic circuit materials can locally be coated with monodisperse PAMA particles (preferable diameter 0.5 to 5 µm). Priming with pegylated cell growth factors allows the growth of specific cell ends. By means of this technology, an exchange of information between tissue, preferably nerve tissue, and intelligent circuits can be achieved.

2) Particles having a Diameter in the Range of 30 to 80 µm:

These particles can be primed with a large number of active substances, enzymes, antibodies, (direct and indirect) antithrombotics, such as hirudin, synthetic, small-molecule thrombin inhibitors, protein C-activating snake poisons, but also with thrombolytics, such as fibrinolase, tPA, streptokinase activator complex etc. These particles are introduced directly into a venovenous (passive) or arteriovenous (active) shunt in miniature "tube columns".

The size of the particles is such that the corpuscular constituents of the blood can pass unhindered. The internal surface of these modules is so large that even intravascular "temporary" systems are possible.

The "multiple" priming of PAMA surfaces makes it possible to induce specific enzymatic reactions in the blood. Thus, leucocytes, monocytes and polymorphonuclear white blood cells can also be specifically altered on the ETS surface (e.g. cleavage of inflammation-specific determinants).

3) Particles having a Diameter in the Range of 80 to 150 µm:

These particle sizes are especially suitable for the gastrointestinal canal or for oral administration. Due to the large internal surface and the unproblematic application for a specific modification of digestive processes, the cholesterol can for example, prior to resorption, be metabolically-chemically modified such that it can no longer or only to a low degree be resorbed. Thus, the entero-hepatic cycle of the cholesterol is interrupted.

The use of surface-bound alcohol dehydrogenases is another important indication for lowering the blood alcohol level.

4) Particles having a Diameter in the Range of 120 to 280 µm:

This particle size is preferably suitable for the oral application of dietary active substances. Due to the large internal surface of the particles an intensive coating with digestionmodifying enzymes is possible (enzymes that break down fat and cholesterol or fat and cholesterol-binding structures). The binding of pegylated alcohol dehydrogenase can reduce the alcohol ingestion in the gastrointestinal canal.

The invention claimed is:

1. A method of binding, cleaving, or otherwise modifying a target substance in a liquid comprising
providing an interactive system comprising:
(a) a surface of a plastic material selected from the group consisting of a poly(meth)acrylate polymer, a polyvinyl ester polymer, copolymers thereof, and a mixture of at least one polyalkyl(meth)acrylate with one or more of the group consisting of polystyrene, polyacrylonitrile, polycarbonate, and polysulfone; the material containing at least one structural element (A) which is the ester group of the acrylate or vinylester polymer, and
(b) a linker coupled to a pharmaceutically or physiologically active substance, the linker selected from the group consisting of a (poly)alkylene glycol, a (poly)alkylene imine, a (poly)alkylene amine, a polyoxazilin and a (poly)alkylene sulfide,
wherein the linker is attached to the structural element (A) on the surface of the plastic material by a hydrogen bond which cannot be reversed by pH values in the range of 2 to 13 or temperatures up to 60° C., and wherein the pharmaceutically or physiologically active substance is capable, to bind, cleave or otherwise modify the target substance; and
contacting the liquid with the interactive system whereby the target substance is bound, cleaved or otherwise modified.

2. The method of claim 1, further comprising removing the substance coupled to the linker from the liquid.

3. The method of claim 1, wherein the liquid is a biological liquid selected from the group consisting of whole blood, plasma, serum, urine, lymph, organ bioptate, enteral contents and sperm.

4. The method of claim 1, wherein the liquid is food or a food component.

5. The method of claim 1, further comprising the interactive system as an extracorporal therapeutic or diagnostic system.

6. The method of claim 1, further comprising using the interactive system application in diagnostic and therapeutic systems for an ailment selected from the group consisting of metabolic diseases, coagulation defects, viral infections, bacterial infections, mycotic infections, parasitic infections and malignant diseases.

7. The method of claim 1, further comprising using the interactive system for the manufacture of dietary food.

8. The method of claim 1, further comprising using the interactive system for production of assay systems.

9. The method of claim 8, wherein the assay systems are selected from the group consisting of affinity columns, microtiter plates, ELISA test plates, microsticks, and diagnostic sticks.

10. The method according to claim 1, wherein the active substance is selected from the group consisting of a protein, a nucleic acid, a cellular signal substance, a partner of a biological or physiological affinity pair, a synthetic nickel-nitrilotriacetic acid (NiNTA) complex, a synthetically produced pharmacon, a synthetically produced active ingredient, and a marker for a biological or synthetic substance.

11. The method according to claim 10, wherein the protein is selected from the group consisting of antigens, antibodies, tumor markers, surface antigens, ligands, receptors, surface-active cell fragments of bacteria, viral proteins and immune messenger substances.

12. The method according to claim 10, wherein the marker is selected from the group consisting of a fluorescent or chemiluminescent substance, an expression sequence code (EST) and an enzyme.

13. The method according to claim 1, wherein the surface is a membrane, a porous or solid microparticle, a magnetic microparticle, a filter mat, a fibrous material, a spun material or a combination thereof, or a coating made from a natural or synthetic substance.

14. The method according to claim 1, wherein the interactive system is comprised within a capillary tube system, a filter for physiological liquids, a dialyzer, a physiological replacement fluid, an enzyme delivery system, an arthroplasty or vascular prosthesis, or an artificial organ.

15. The method according to claim 1, wherein the active substance is selected from the group consisting of an anticoagnlant, a metabolically active enzyme, an antibiotic and a synthetic pharmacon.

16. The method according to claim 15, wherein the anticoagulant is selected from the group consisting of heparin, hirudin, directly acting antithrombins and prothrombin.

17. The method according to claim 1, wherein the active substance further comprises An agent selected form an enzyme and a pharmaceutical composition.

18. A kit comprising an interactive system for carrying out a method of binding, cleaving, or otherwise modifying a target substance in a liquid comprising contacting a liquid with an interactive system comprising:
(a) a surface of a plastic material selected from the group consisting of a poly(meth)acrylate polymer, a polyvinyl ester polymer, copolymers thereof, and a mixture of at least one polyalkyl(meth)acrylate with one or more of the group consisting of polystyrene, polyacrylonitrile, polycarbonate, and polysulfone; the material containing at least one structural element (A) which is the ester group of the acrylate or vinylester polymer, and
(b) a linker coupled to a pharmaceutically or physiologically active substance, the linker selected from the group consisting of a (poly)alkylene glycol, a (poly)alkylene imine, a (poly)alkylene amine, a polyoxazilin and a (poly)alkylene sulfide,
wherein the linker is attached to the structural element (A) on the surface of the plastic material by a hydrogen bond which cannot be reversed by pH values in the range of 2 to 13 or temperatures up to 60° C., wherein the target substance is bound, cleaved or otherwise modified by the coupled substance; wherein the kit comprises items selected from the group consisting of suitable reagents, buffer solutions, reaction vessels, packaging and combinations thereof.

* * * * *